United States Patent
Aydelotte

(10) Patent No.: US 9,962,518 B2
(45) Date of Patent: May 8, 2018

(54) TIME-SENSITIVE CATHETER ALARM

(71) Applicant: The Board of Regents of The University of Texas System, Austin, TX (US)

(72) Inventor: Jayson Aydelotte, San Antonio, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 174 days.

(21) Appl. No.: 15/070,229

(22) Filed: Mar. 15, 2016

(65) Prior Publication Data

US 2016/0361516 A1 Dec. 15, 2016

Related U.S. Application Data

(63) Continuation of application No. 13/745,368, filed on Jan. 18, 2013, now abandoned.

(60) Provisional application No. 61/587,953, filed on Jan. 18, 2012.

(51) Int. Cl.
*A61M 25/00* (2006.01)

(52) U.S. Cl.
CPC ...... *A61M 25/002* (2013.01); *A61M 25/0017* (2013.01); *A61M 2205/18* (2013.01); *A61M 2205/33* (2013.01); *A61M 2205/3306* (2013.01); *A61M 2205/502* (2013.01); *A61M 2205/581* (2013.01); *A61M 2205/587* (2013.01)

(58) Field of Classification Search
CPC ...... A61M 25/0017; A61M 2025/0019; A61M 2205/13; A61M 2205/17; A61M 2205/33; A61M 2205/3303; A61M 2205/3317; A61M 2210/1078; A61M 2210/1089; A61M 2210/1085
See application file for complete search history.

(56) References Cited

U.S. PATENT DOCUMENTS

| | | | |
|---|---|---|---|
| 4,588,303 A | 5/1986 | Wirtschafter et al. | |
| 5,259,838 A | 11/1993 | Taylor et al. | |
| 5,583,832 A | 12/1996 | Deponty | |
| 6,377,848 B1 | 4/2002 | Garde et al. | |
| 7,382,692 B1 | 5/2008 | Hildebrandt | |
| 7,785,299 B2 | 8/2010 | Crawford et al. | |
| 2005/0256447 A1 | 11/2005 | Richardson et al. | |
| 2006/0265031 A1 | 11/2006 | Skwarek et al. | |
| 2007/0147942 A1* | 6/2007 | Sojka | A47L 25/08 401/7 |
| 2008/0177159 A1 | 7/2008 | Gavriely | |
| 2008/0278336 A1 | 11/2008 | Ortega et al. | |
| 2009/0163111 A1 | 6/2009 | Garbos et al. | |

(Continued)

FOREIGN PATENT DOCUMENTS

GB 2395128 5/2004

*Primary Examiner* — Tatyana Zalukaeva
*Assistant Examiner* — Kai Weng
(74) *Attorney, Agent, or Firm* — Meyertons, Hood, Kivlin, Kowert & Goetzel, P.C.; Mark R. DeLuca

(57) ABSTRACT

A catheter includes an elongated tube, wherein a portion of the elongated tube is positionable inside the body of a subject such that, during use, bodily fluids travel from the subject through the elongated tube. A timing device is coupled to the elongated tube, wherein, after the catheter is inserted into the body of the subject, the timing device provides an indication of the amount of time that the catheter has been disposed inside the subject.

12 Claims, 4 Drawing Sheets

(56) References Cited

U.S. PATENT DOCUMENTS

2009/0198182 A1    8/2009   Fujishima et al.
2011/0004153 A1    1/2011   Kipping
2011/0130728 A1    6/2011   McKinnon

* cited by examiner

TIME-SENSITIVE CATHETER ALARM

PRIORITY CLAIM

This application is a continuation application of U.S. patent application Ser. No. 13/745,368 entitled "TIME-SENSITIVE CATHETER ALARM" filed Jan. 18, 2013, which claims priority to U.S. Provisional Application Ser. No. 61/587,953 entitled "TIME-SENSITIVE CATHETER ALARM" filed Jan. 18, 2012, both of which are incorporated herein by reference in its entirety.

BACKGROUND OF THE INVENTION

1. Field of the Invention

The invention generally relates to catheters.

2. Description of the Relevant Art

A catheter is a tube that can be inserted into a body cavity, duct, or vessel, that allow drainage, administration of fluids or gases, or access by surgical instruments. The process of inserting a catheter is catheterization. In most uses, a catheter is a thin, flexible tube though in some uses, it is a larger, solid catheter. A catheter left inside the body, either temporarily or permanently, may be referred to as an indwelling catheter.

An example of a catheter is a Foley catheter. A Foley catheter is a flexible tube that is passed through the urethra and into the bladder. The tube has two separated channels, or lumens, running down its length. One lumen is open at both ends, and allows urine to drain out into a collection bag. The other lumen has a valve on the outside end and connects to a balloon at the tip; the balloon is inflated with sterile water when it lies inside the bladder, in order to stop it from slipping out. Foley catheters are commonly made from silicone rubber or natural rubber.

A major problem with Foley catheters is that they have a tendency to contribute to urinary tract infections (UTI). This occurs because bacteria can travel up the catheters to the bladder where the urine can become infected. To combat this, the industry is moving to antiseptic coated catheters. This has been helpful, but it has not completely solved this major problem. An additional problem is that Foley catheters tend to become coated over time with a biofilm that can obstruct the drainage. This increases the amount of stagnant urine left in the bladder, which further contributes to the problem of urinary tract infections. When a Foley catheter becomes clogged, it must be flushed or replaced.

The Center for Medicare and Medicaid are following several guidelines for proper in-patient health care on an epidemiologic basis for catheters. In recommendations from the Center, Foley catheters must be pulled within 48 hours of insertion or a doctor needs to document why the Foley is being left in. This is a nationwide movement and many hospitals are developing many different protocols to alert the nurse/physician team to pull the catheter or leave a note. It is therefore desirable to have an easy to implement protocol which will allow hospital staff to easily determine the length of time that a catheter has been in place.

SUMMARY OF THE INVENTION

In one embodiment, a catheter system includes: an elongated tube, wherein a portion of the elongated tube is positionable inside the body of a subject such that, during use, bodily fluids travel from the subject through the elongated tube; a collection container coupled to the elongated tube, wherein bodily fluids from the subject are collected in the collection device; and a timing device coupled to a portion of the catheter system, wherein, after the catheter is inserted into the body of the subject, the timing device provides an indication of the amount of time the catheter has been disposed inside the subject. The timing device may be connected directly to the elongated tube or to the collection system. In an embodiment, the catheter is a catheter for draining urine from the bladder of the subject.

In an embodiment, the elongated tube comprises a distal end and a proximal end, the distal end being positionable inside the body of a subject during use, and the proximal end being coupleable to a collection container such that, during use, the bodily fluids travel through elongated tube to the collection container.

The timing device may include a light that provides a visual signal that indicates the amount of time that the catheter has been disposed inside the subject. In an embodiment, the light is an LED light. The LED light may produce pulses of light, the frequency of the pulses of light providing a visual indication of the amount of time that the catheter has been disposed inside the subject. In an embodiment, the timing device includes a light that provides different colors of light, each color representing a predetermined amount of time that the catheter has been disposed inside the subject. The timing device may provide an audio signal that indicates the amount of time that the catheter has been disposed inside the subject. The timing device may also include a display indicating the amount of time that the catheter has been disposed inside the subject.

In some embodiments, the timing device produces a signal that indicates that the catheter needs to be removed from the subject. The timing device may include a blinking light, wherein the blinking light provides pulses of light at a frequency that is representative of the amount of time that the catheter has been disposed inside the subject. The timing device may produce pulses of light at increasing frequency the longer the catheter is disposed in the subject.

The timing device, in some embodiments, includes an activation device. The activation device may provide a signal to activate a controller of the timing device to begin measuring the elapsed time. In an embodiment, the activation device comprises a pull strip, wherein removal of the pull strip from the timing device causes a signal to be produced that activates the controller. In another embodiment, the activation device comprises a magnetic contact coupled to the timer, wherein removal of the magnetic contact causes a signal to be produced that activates the controller.

A method of removing bodily fluids from a subject with a catheter may include: inserting a distal portion of a catheter system into a subject, the catheter system comprising: an elongated tube, wherein a portion of the elongated tube is positionable inside the subject such that, during use, bodily fluids travel from the subject through the elongated tube; a collection container coupled to the elongated tube, wherein bodily fluids from the subject are collected in the collection device; and a timing device coupled to a portion of the catheter system, wherein, after the catheter is inserted into the body of the subject, the timing device provides an indication of the amount of time the catheter has been disposed inside the subject; and activating the timing device.

In an embodiment, a catheter includes: an elongated tube, wherein a portion of the elongated tube is positionable inside the body of a subject such that, during use, bodily fluids travel from the subject through the elongated tube; and a timing device coupled to the elongated tube, wherein, after the catheter is inserted into the body of the subject, the timing device provides an indication of the amount of time the catheter has been disposed inside the subject.

In an embodiment, a collection container for use with a catheter is couplable to the catheter such that bodily fluids from a subject are collected in the collection device via the catheter. The collection container includes a timing device coupled to a portion of the collection device, wherein, after the collection device is used to collect fluids from the subject, the timing device provides an indication of the amount of time the collection device has been in use.

In an embodiment, a timing device is couplable to a biomedical device, wherein, after the biomedical device is used on the subject, the timing device provides an indication of the amount of time the biomedical device has been in use.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
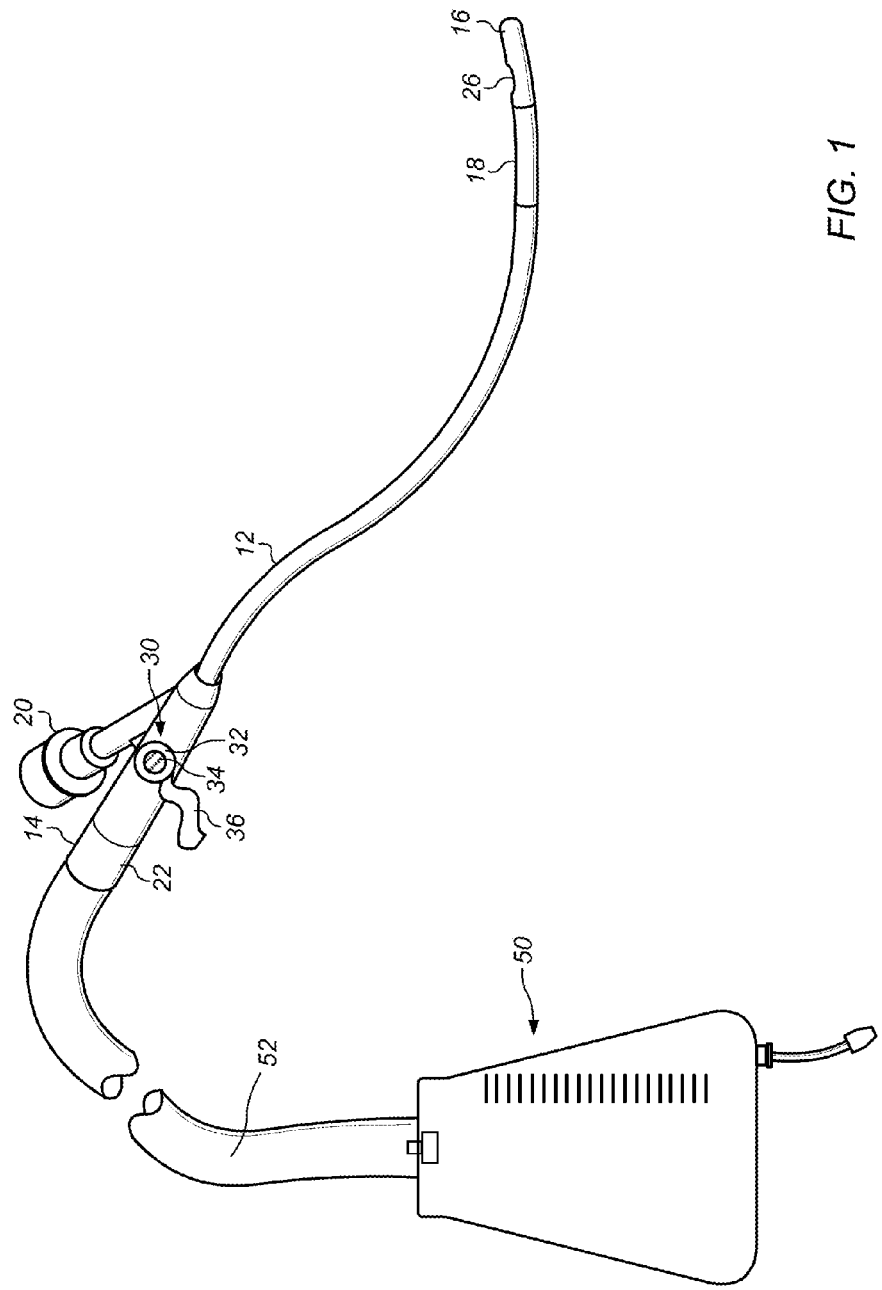
FIG. 1 depicts an embodiment of a catheter system that includes a timer coupled to a drainage port of the catheter.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

The above-described deficiencies of the prior art by a catheter that includes a timing device that provides an indication of the amount of time the catheter has been in use. In one embodiment, a catheter includes an elongated tube comprising a distal end and a proximal end. The distal end is positionable inside the body of a subject during use. The proximal end is coupleable to a collection container such that, during use, bodily fluids travel from the subject, through the elongated tube to the collection container. A timing device is coupled to the elongated tube. After the catheter is inserted into the body of the subject, the timing device provides an indication of the amount of time that the distal end of the catheter has been disposed inside the subject.

Figure 4:
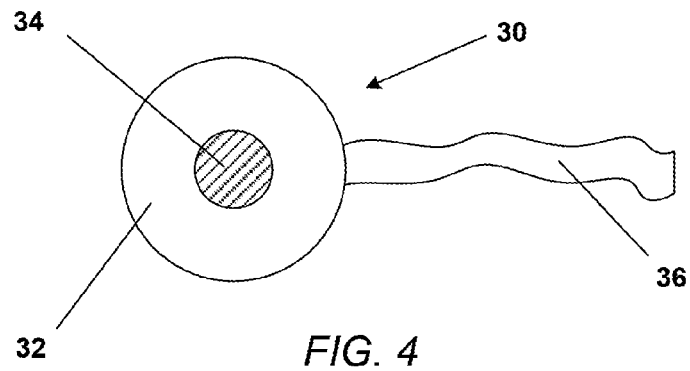
FIG. 4 depicts an embodiment of a timer with an activation strip.
Figure 5:
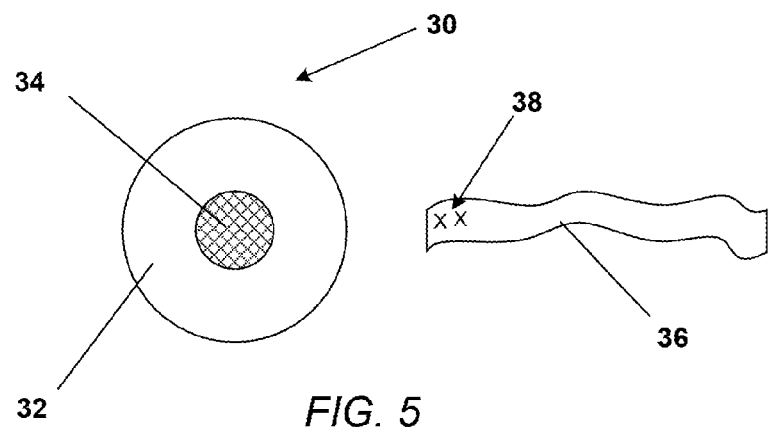
FIG. 5 depicts an embodiment of a timer with the activation strip removed.

In one embodiment, the catheter is a Foley catheter. FIG. 1 depicts a projection view of a Foley catheter that includes a timing device. FIGS. 4 and 5 depict various views of the timing device. A Foley catheter is a catheter that is generally used for draining urine from the bladder of a subject. A Foley catheter includes an elongated tube 12. The elongated tube includes a distal end 16 and a proximal end 14. During use, distal end 16 is passed through the subject's urethra and into the bladder. Distal end 16 includes an opening 26 through which the urine passes from the subject's bladder into the tube 12. A balloon 18 is also positioned at the distal end of the catheter. During use the balloon is inflated with a fluid (e.g., sterile water) when it lies inside the bladder. The inflated balloon inhibits the catheter from slipping out after the catheter is inserted into the bladder.

Elongated tube 12, includes two lumens running along the length of the tube. A first lumen is open at both ends, and allows urine to drain out into a collection container. The second lumen (not shown) has a valve 20 at proximal end 14 and connects to balloon 18 at distal end 16. A fluid is passed through valve 20, into balloon 18, inflating the balloon. The fluid may be a gas (e.g., air or nitrogen) or a liquid (e.g., sterile water or saline).

Proximal end 14 also includes a urine drainage port 22. During use, urine drainage port 22 is coupled to a collection container 50 (e.g. a urometer) using conduit 52. Urine passing through the elongated tube from the subject's bladder passes through the drainage port 22 into collection container 50. In some embodiments, a drainage port comprises a quick disconnect portion to allow the collection container to be quickly replaced.

A timing device 30 may be coupled to the catheter. Timing device 30 may be connected to the drainage port 22 as shown. In other embodiments, timing device 30 may be connected to elongated tube 12 or valve 20. Generally, timing device 30 may be coupled to any portion of the catheter that is not disposed inside the subject's body. Preferably, the timing device is positioned on a readily accessible portion of the catheter.

Figure 2:
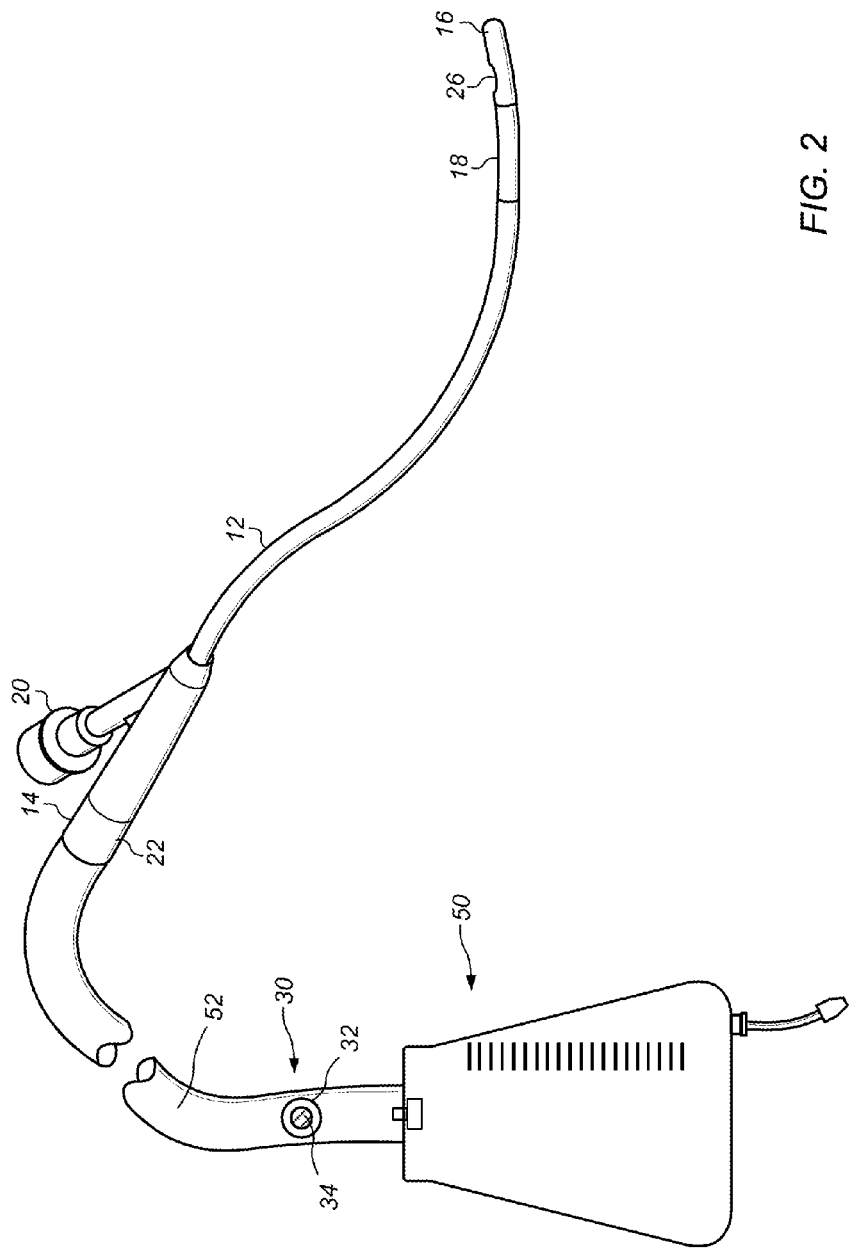
FIG. 2 depicts an embodiment of a catheter system that includes a timer coupled to an elongated tube of the catheter.
Figure 3:
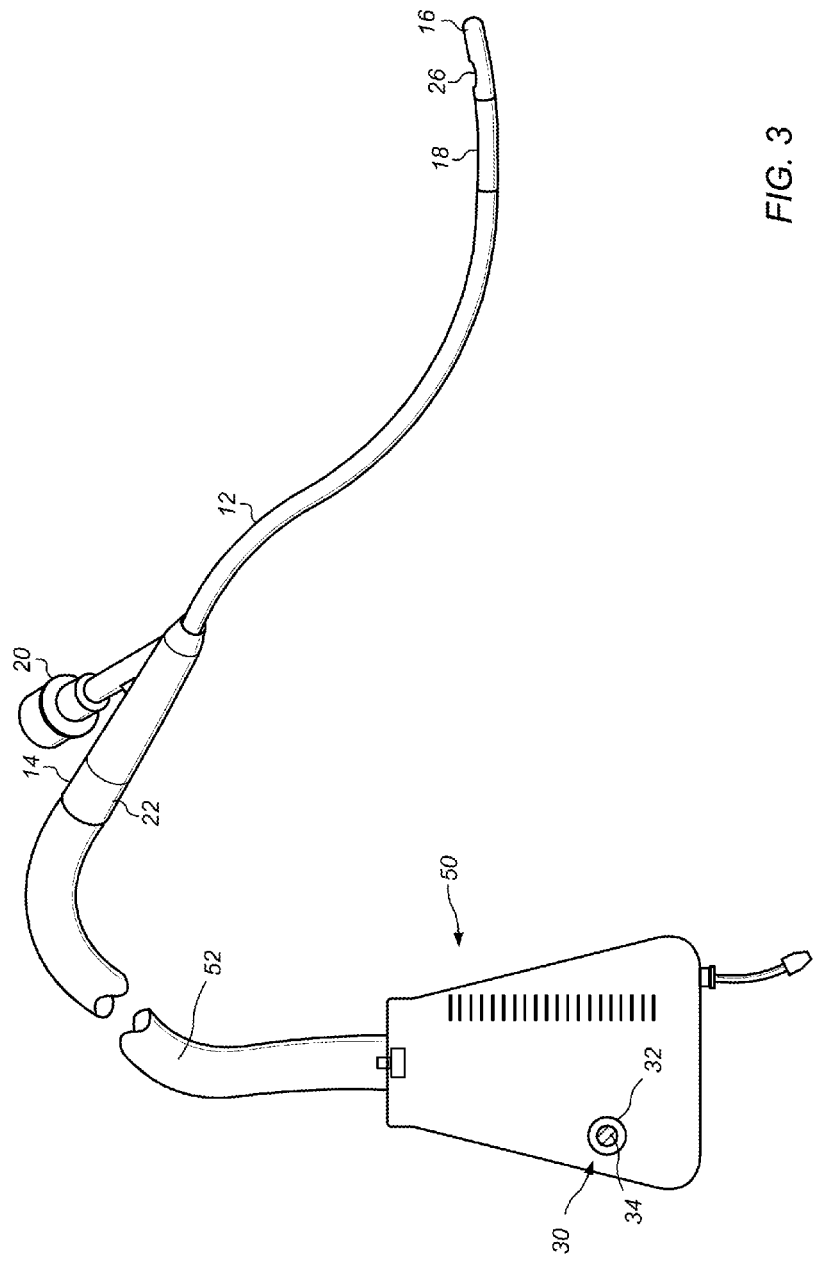
FIG. 3 depicts an embodiment of a catheter system that includes a timer coupled to a collection container.

In an alternate embodiment, timing device 30 may be coupled to conduit 52 (as depicted in FIG. 2) or to collection container 52 (as depicted in FIG. 3). Generally, collection container 50 and the portion of conduit 52 near the collection container are readily visible to the provider. Placing timing device 30 on the conduit or collection container may allow a provider to more readily determine the status of the catheter without having to access the catheter.

In one embodiment, timing device 30 is a light that provides a visual signal that indicates the amount of time that the distal end of the catheter has been disposed inside the subject. In one embodiment, timing device 30 includes a housing base 32 and a light 34 coupled to the housing base. Light 34 may be any kind of light including an incandescent light, a fluorescent light, or an LED light. LED lights may be particularly useful since they have low power requirements.

Disposed in housing base 32 are a power supply and a controller. Power supply supplies power to the controller and the light. Power supply, in some embodiments, is a battery (e.g., a button cell battery). The controller is programmed to begin recording an elapsed time when a timer signal is received. Controller is also programmed to produce an indication of the elapsed time that a provider of the catheter may use to determine the length of time that the catheter has been disposed in the subject.

When a light is coupled to the timing device, the controller may use a variety of signals to let the provider know the elapsed time that the catheter has been in use. In one embodiment, the controller sends power to the light to produce pulses of light. The frequency of the pulses of light may provide a visual indication of the amount of time that the catheter has been disposed inside the subject. In one exemplary example, the controller causes the light to begin blinking at a first rate 36 hours after initial insertion of the Foley Catheter. The light will blink at an increasing frequency until the 48 hour mark. After the 48 hour mark, the light will stay continuously lit. The controller will turn the light off at 54 hours.

Other indication schemes may be used. In another embodiment, the timing device includes one or more light sources that may be used to provide different colors of light. Each color of light may represent a predetermined amount of time that the catheter has been in use. For example, the timing device may display a green light (pulsed or continuous) during the first 36 hours of use. After 36 hours have elapsed, the timing device may display a yellow light (pulsed or continuous) indicating that the time to remove the catheter is approaching. After 48 hours have elapsed the timing device may display a red light, indicating that the catheter has been in the subject for more than 48 hours.

In another embodiment, timing device may provide an audio alert along with, or instead of, a light signal to provide an indication of the amount of time that the catheter has been in use. An audio alert may be provided periodically or continuously. In one embodiment, an audio alert is provided when the catheter is to be removed, due to the expiration of a predetermined amount of time. The audio signal may be pulsed or continuous.

In another embodiment, the timing device may include a display. The display may be an LED or an LCD display. The display may depict the time that has elapsed since the catheter was placed into the subject. In an alternate embodiment, the display may depict the amount of time that the catheter may be left in the patient. In either embodiment, the display may be continuously updated (e.g., every second or every minute).

In some embodiments, a timing device may use one or more of the above described methods of indicating the amount of time that the catheter has been disposed in the subject. The timing device may include any combination of lights, audio alerts, and digital displays.

In an embodiment, timing device 30 includes an activation device 36. Activation device 36 is used by the provider to activate the timer of controller of the timing device to begin measuring the elapsed time. In one embodiment, the activation device comprises a pull strip 36 that causes a signal to be produced that activates the controller. In one embodiment, pull strip 36 is formed from an electrically insulating material and is positioned between two electrical contacts. When pull strip 36 is removed from the timing device, the two electrical contacts may come into contact with each other and activate the controller. In an alternate embodiment, pull strip 36 may include one or more magnetic contacts 38 which are coupled to a magnetic contact (not shown) disposed in the timing device. When pull strip 36 is removed, magnetic contacts 38 are displaced from the timing device, causing the controller to be activated. Other activation devices may be used such as switches (buttons, toggle switches, etc).

In one embodiment, the activation device is removed by the provider when the catheter is placed in the subject, causing the timing device to become activated. Alternatively, the activation device may be automatically activated when the catheter is removed from the sterile packaging the catheter is stored in. In one exemplary embodiment, the activation device is a pull strip. The pull strip may be secured to a portion of the catheter's sterile packaging such that when the catheter is removed from the packaging, the pull strip remains attached to the packaging, causing the timing device to become activated without the providers intervention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A catheter system comprising:
    an elongated tube, wherein a portion of the elongated tube is configured to be positioned inside the body of a subject such that, during use, bodily fluids travel from the subject through the elongated tube;
    a collection container coupled to the elongated tube, wherein the collection device is configured to collect bodily fluids from the subject; and
    a timing device coupled to a portion of the catheter system;
    an activation device coupled to the timing device; wherein the activation device provides a signal to activate a controller of the timing device to begin measuring an elapsed time;
    packaging surrounding the elongated tube and/or the timing device, wherein removal of the packaging from the elongated tube and/or the timing device causes the activation device to activate the controller of the timing device to begin measuring the elapsed time;
    wherein the activation device comprises a pull strip, wherein removal of the pull strip from the timing device causes a signal to be produced that activates the controller, and
    wherein a portion of the pull strip is coupled to the packaging such that removal of the packaging from the elongated tube and/or the timing device removes the pull strip from the timing device; and
    wherein the timing device provides an indication of the amount of time the catheter has been removed from the packaging.

2. The catheter system of claim 1, wherein the elongated tube comprises a distal end and a proximal end, the distal end is configured to be positioned inside the body of the subject during use, and the proximal end being coupleable to the collection container such that, during use, the bodily fluids travel through elongated tube to the collection container.

3. The catheter system of claim 1, wherein the catheter is for draining urine from the bladder of the subject.

4. The catheter of system claim 1, wherein the timing device is a light that provides a visual signal that indicates the amount of time that the catheter has been removed from the packaging.

5. The catheter of system claim 1, wherein the timing device provides an audio signal that indicates the amount of time that the catheter has been removed from the packaging.

6. The catheter of system claim 1, wherein the timing device comprises a display indicating the amount of time that the catheter has been removed from the packaging.

7. The catheter of system claim 1, wherein the timing device is connected to the elongated tube.

8. The catheter of system claim 1, wherein the timing device is connected to the collection container.

9. The catheter of system claim 1, wherein the pull strip comprises a pull strip magnetic contact coupled to a timer magnetic contact, wherein removal of the packaging from the elongated tube and/or the timing device separates the pull strip magnetic contact from the timer magnetic contact.

10. The catheter of system claim 1, wherein the timing device produces an indication that indicates that the catheter needs to be removed from the subject.

11. A method of removing bodily fluids from a subject with a catheter comprising:
obtaining a catheter system, the catheter system comprising:
an elongated tube, wherein a portion of the elongated tube is configured to be positioned inside the subject such that, during use, bodily fluids travel from the subject through the elongated tube;
a collection container coupled to the elongated tube, wherein the collection device is configured to collect bodily fluids from the subject;
a timing device coupled to a portion of the catheter system;
an activation device coupled to the timing device; wherein the activation device provides a signal to activate a controller of the timing device to begin measuring an elapsed time; and
packaging surrounding the elongated tube and/or the timing device, wherein removal of the packaging from the elongated tube and/or the timing device causes the activation device to activate the controller of the timing device to begin measuring the elapsed time;
wherein the activation device comprises a pull strip, wherein removal of the pull strip from the timing device causes a signal to be produced that activates the controller, and wherein a portion of the pull strip is coupled to the packaging such that removal of the packaging from the elongated tube and/or the timing device removes the pull strip from the timing device;
removing the packaging from the catheter system, wherein removal of the packaging activates the timing device, wherein the timing device provides an indication of the amount of time the catheter has been removed from the packaging; and
inserting a distal portion of the elongated tube into the subject.

12. A catheter comprising:
an elongated tube, wherein a portion of the elongated tube is configured to be positioned inside the body of a subject such that, during use, bodily fluids travel from the subject through the elongated tube;
a timing device coupled to the elongated tube;
an activation device coupled to the timing device; wherein the activation device provides a signal to activate a controller of the timing device to begin measuring an elapsed time; and
packaging surrounding the elongated tube, wherein removal of the packaging from the elongated tube causes the activation device to activate the controller of the timing device to begin measuring the elapsed time;
wherein the activation device comprises a pull strip, wherein removal of the pull strip from the timing device causes a signal to be produced that activates the controller, and wherein a portion of the pull strip is coupled to the packaging such that removal of the packaging from the elongated tube and/or the timing device removes the pull strip from the timing device; and
wherein the timing device provides an indication of the amount of time the catheter has been removed from the packaging.

* * * * *